(12) United States Patent
Crangle

(10) Patent No.: US 11,109,847 B2
(45) Date of Patent: Sep. 7, 2021

(54) METHODS AND APPARATUS FOR CONCURRENTLY DETECTING AND TREATING MEDICAL CONDITIONS OF A BODY

(71) Applicant: Richard N. Crangle, Salt Lake City, UT (US)

(72) Inventor: Richard N. Crangle, Salt Lake City, UT (US)

( * ) Notice: Subject to any disclaimer, the term of this patent is extended or adjusted under 35 U.S.C. 154(b) by 0 days.

(21) Appl. No.: 17/061,270

(22) Filed: Oct. 1, 2020

(65) Prior Publication Data

US 2021/0093306 A1    Apr. 1, 2021

Related U.S. Application Data

(60) Provisional application No. 62/909,102, filed on Oct. 1, 2019.

(51) Int. Cl.
| | | |
|---|---|---|
| A61B 17/42 | (2006.01) |
| A61B 1/303 | (2006.01) |
| A61B 10/02 | (2006.01) |
| A61B 1/32 | (2006.01) |
| A61B 1/018 | (2006.01) |
| A61B 18/02 | (2006.01) |
| A61B 17/02 | (2006.01) |
| A61B 17/3205 | (2006.01) |
| A61B 18/00 | (2006.01) |

(52) U.S. Cl.
CPC .......... *A61B 10/0291* (2013.01); *A61B 1/018* (2013.01); *A61B 1/303* (2013.01); *A61B 1/32* (2013.01); *A61B 17/0218* (2013.01); *A61B 17/3205* (2013.01); *A61B 17/42* (2013.01); *A61B 18/02* (2013.01); *A61B 2018/00559* (2013.01)

(58) Field of Classification Search
CPC .......... A61B 1/32; A61B 1/303; A61B 1/018; A61B 17/3205; A61B 17/02; A61B 17/42; A61B 17/0218; A61B 17/0281; A61B 17/12013; A61B 17/1285; A61B 2018/00559; A61B 18/02; A61B 10/02; A61B 10/0291
See application file for complete search history.

(56) References Cited

U.S. PATENT DOCUMENTS

2013/0211321 A1*  8/2013  Dubois ................. A61M 13/00
                                                     604/26
2020/0187769 A1*  6/2020  Rahimian .............. A61B 1/303

* cited by examiner

*Primary Examiner* — Vi X Nguyen
(74) *Attorney, Agent, or Firm* — Morriss O'Bryant Compagni Cannon, PLLC

(57) ABSTRACT

Methods provide for the concurrent evaluation, detection and treatment of actual or potential medical conditions at a site of a body, and are particularly directed to medical procedures and concurrent treatment of areas of the body that are difficult to visualize; and a kit providing apparatus for carrying out evaluation, detection and real-time treatment of the site of a body for actual or potential medical conditions is disclosed.

8 Claims, 3 Drawing Sheets

US 11,109,847 B2

METHODS AND APPARATUS FOR CONCURRENTLY DETECTING AND TREATING MEDICAL CONDITIONS OF A BODY

CROSS-REFERENCE TO RELATED APPLICATION

This application claims priority to U.S. Provisional Application Ser. No. 62/909,102 filed on Oct. 1, 2019, the entirety of which is incorporated by this reference.

TECHNICAL FIELD

This invention relates to methods for detecting and concurrently treating medical conditions of a body, particularly in areas of a body that are readily obscured from direct visualization.

BACKGROUND OF THE INVENTION

It is necessary in the rendering of medical procedures to evaluate certain areas of the body for the presence of a medical condition, whether actual or potential, that needs to be monitored or treated. Some of the areas of the body are not readily visible and require the use of certain instrumentation, such as endoscopes, to conduct the needed procedure.

With respect to certain procedures, it is typical to perform an initial procedure merely to determine if a medical condition exists, or potentially exists. Such procedures may typically involve taking a tissue sample or biopsy of the potentially affected site of the body. The initial procedure is then completed, once the tissue sample or biopsy is taken from the patient, and the patient must leave the medical facility to await a lab report determination of the presence or absence of a suspected condition. In such situations, the patient is subjected to a waiting period that may cause anxiety, and the patient may then need to be subjected to another time-consuming and painful procedure to treat a condition if one is detected. Moreover, the time span between diagnosis and treatment of lesions may allow cancerous cells to spread within the body and colonize in various organs.

Such procedures of taking cell samples and sending the cell samples to a lab to determine a condition are common in Pap test to determine the presence of cervical cancer. The most common Pat test procedure is the Thinprep Pap test, which accounts for more than 99% of pap tests. The Thinprep Pap test includes the following steps:
1. Assemble collection devices and Thinprep Pap test vial.
2. Obtain an adequate sampling of the ectocervix using a spatula.
3. Rinse the spatula into the solution vial by swirling the spatula vigorously in the vial 10 times. Discard the spatula.
4. Obtain an adequate sampling from the endocervix using an endocervical brush device. Insert the brush into the endocervical canal until only the bottom-most fibers are exposed and slowly rotate ¼ or ½ turn in one direction.
5. Rinse the brush in the solution vial by rotating the device in the solution 10 times while pushing against the vial wall. Swirl the brush vigorously to further release material. Discard the brush.
6. Tighten the cap so that the torque line on the cap passes the torque line on the vial.
7. Record the patient's name and history number on the vial or attach a printed patient identification label.
8. Send labeled specimen vial and completed request form to the laboratory for processing.

Lab tests are then conducted on the specimen to determine whether the collected cells are cancerous. This process typically takes 1 to 3 weeks. Once positive lab results are returned to the attending physician, the patient must then schedule an appointment for treatment.

Accordingly, the foregoing standard procedure for collecting a sample via a Pap smear test requires the patient to wait to receive results and return to the doctor's office or other medical facility if a cancer is detected. Moreover, once the patient returns, additional procedures are conducted on the patient at that time to remove any cancerous lesions or cells. However, between the time when the Pap test is conducted and the patient is able to return seek treatment, the cancer cells will continue to proliferate. Therefore, one of the medical advantages of immediate treatment is to prevent such pathogens from proliferating.

Such screening procedures, for the early detection of premalignant or cancerous lesions of the cervix, however, are expensive and technically difficult, especially in resource-challenged settings. Additionally, Pap tests are only about 70% accurate in detection of premalignant lesions of the cervix. Thus, there is a need for less expensive and at least equally effective alternative screening methods for premalignant or cancerous lesions of the cervix.

The ability to concurrently detect and treat an actual or potential medical condition, such as cancerous cells on the cervix, would reduce anxiety for a patient since the patient could undergo the detection phase of the procedure followed immediately by treatment, thus limiting the procedure to a single event. Methods of concurrently detecting and treating a medical condition would also reduce the time that a patient must spend in attending to the treatment of a medical condition, and medical costs would be reduced in terms of shorter medical staff time and equipment costs.

SUMMARY OF THE INVENTION

In a first aspect, embodiments are disclosed of methods for concurrent detection and treatment of actual or potential medical conditions of a body, comprising placing a guide device in proximity to a site of a body to be evaluated for detection of actual or potential medical conditions, placing a detection device in proximity to the site of the body to be evaluated using the guide device to aid placement of the detection device, determining the presence of an actual or potential medical condition at the site that is concurrently treatable, placing a treatment device at the site using the guide device for placement of the treating device in proximity to the site, treating the site of detected actual or potential medical condition and removing the treatment device and guide device from the site following treatment.

In certain embodiments, the methods further comprise contacting the site of the body with a detector material selected to detect one or more actual or potential medical conditions at the site following the placing of the detection device in proximity to the site.

In other certain embodiments, the detector material is a flowable substance deliverable to the site by directing the substance to or on the site by operation of the detection device.

In yet other embodiments, the detection device comprises a tubular member having a swab attached at one end thereof.

In still other embodiments, the tubular member has a lumen for delivering one or more substances through the lumen to the swab.

In some embodiments, the detection device is a scope having a visualization element for visualizing the site in real-time.

In certain embodiments, the treatment device is structured with a cutting tool at one end for contacting the site and excising material or tissue from the site in response to detection of an actual or potential medical condition at the site.

In certain other embodiments, the treatment device is a cryogenic tool being configured to deliver a cryogenic substance to the site for treating an actual or potential medical condition at the site.

In some embodiments, the guide device comprises a cannula portion for passing instruments therethrough to the site of the body.

In a second aspect, methods of evaluating and treating actual or potential gynecological conditions in real-time comprise providing a spiral cervical retractor device, such as the spiral cervical retractor apparatus disclosed in U.S. Pat. No. 6,537,285 (the entirety of which is incorporated by this reference), positioning the spiral cervical retractor device in place in proximity to a site for evaluation of actual or potential gynecological conditions, positioning a detection device in proximity to the site for evaluation of the presence of actual or potential gynecological conditions, determining the presence of an actual or potential gynecological condition, positioning a treatment device in proximity to the site to treat detected gynecological conditions that are concurrently treatable, treating detected gynecological conditions sequentially following detection of such conditions, removing the treating device from the site and removing the spiral cervical retractor device.

In some embodiments, the methods further comprise providing and placing a speculum for facilitation of placement of the spiral retractor device.

In other embodiments, the spiral cervical retractor is used to guide placement of the detection device and the treating device.

In yet other embodiments, determining the presence of actual or potential gynecological conditions at the site is carried out by use of an optical visualization device.

In certain other embodiments, determining the presence of actual or potential gynecological conditions at the site is carried out by application of an indicator substance that indicates the presence of actual or potential gynecological conditions.

In some embodiments, the detection device comprises a tubular member having a swab attached at one end thereof.

In other embodiments, the tubular member has a lumen for delivering one or more substances through the lumen to the swab.

In certain embodiments, the lumen is prefilled with one or more substances for detecting or treating a gynecological condition at the site.

In certain other embodiments, the treatment device is structured with a cutting tool at one end for contacting the site and excising material from the site in response to detection of an actual or potential gynecological condition at the site.

In yet other embodiments, the treatment device is a cryogenic tool configured to deliver a cryogenic substance to the site for treating an actual or potential gynecological condition at the site.

In a third aspect, a kit for evaluating and concurrently treating gynecological conditions comprises, in combination, a spiral cervical retractor device, a detection device to provide detection of one or more gynecological conditions for treatment and a container for retaining the spiral cervical retractor device and detection device.

In some embodiments, the kit further comprises a treatment device for treating detected gynecological conditions in use.

In certain embodiments, the detection device comprises a contact device for applying substances to in situ tissue to determine the presence of gynecological conditions.

In other embodiments, the kit further comprises substances for combination in delivering an indicator material to in situ tissue for determination of the presence of gynecological conditions.

In yet other embodiments, the kit further comprises substances directed to treating a detected gynecological condition in use.

In other embodiments, the kit further comprises a speculum.

Other aspects, features, and advantages will become apparent from the following detailed description when taken in conjunction with the accompanying drawings, which are a part of this disclosure and which illustrate, by way of example, principles of the inventions disclosed.

BRIEF DESCRIPTION OF THE DRAWINGS

When considered in connection with the following illustrative figures, a more complete understanding of the present invention may be derived by referring to the detailed description. In the figures, like reference numbers refer to like elements or acts throughout the figures. Various embodiments of the present invention are shown and described in reference to the numbered drawings.

DETAILED DESCRIPTION OF THE INVENTION

Figure 1:
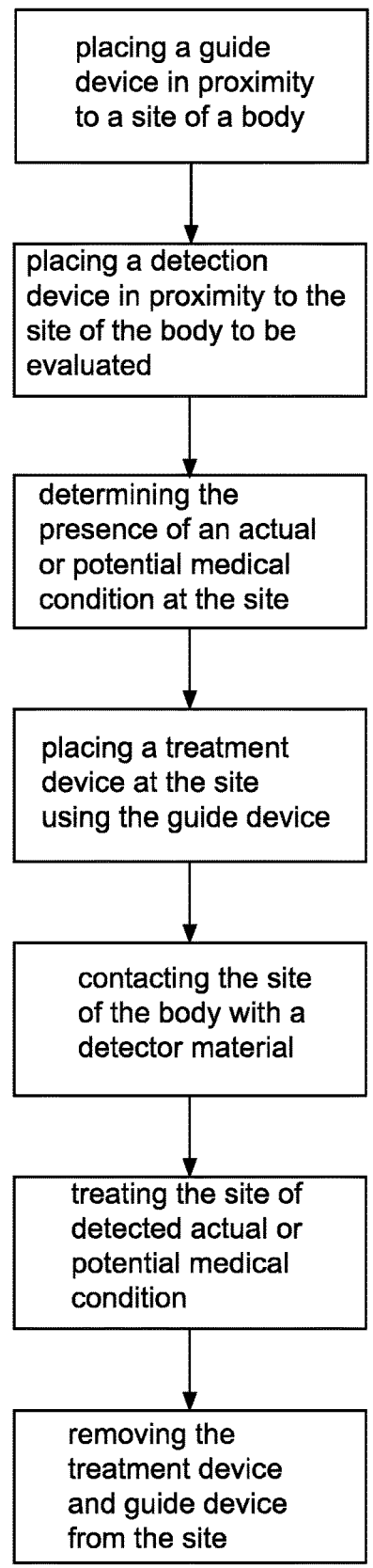
FIG. 1 is a schematic flow diagram of a first embodiment of a method for concurrent detection and treatment of actual or potential medical conditions of a body in accordance with the principles of the present invention.

The invention and accompanying drawings will now be discussed in reference to the numerals provided therein so as to enable one skilled in the art to practice the present invention. The drawings and descriptions are exemplary of various aspects of the invention and are not intended to narrow the scope of the appended claims. Unless specifically noted, it is intended that the words and phrases in the specification and the claims be given their plain, ordinary, and accustomed meaning to those of ordinary skill in the applicable arts. It is noted that the inventor can be his own lexicographer. The inventor expressly elects, as his own lexicographer, to use only the plain and ordinary meaning of terms in the specification and claims unless they clearly state otherwise and then further, expressly set forth the "special"

definition of that term and explain how it differs from the plain and ordinary meaning. Absent such clear statements of intent to apply a "special" definition, it is the inventor's intent and desire that the simple, plain and ordinary meaning to the terms be applied to the interpretation of the specification and claims.

The inventors are also aware of the normal precepts of English grammar. Thus, if a noun, term, or phrase is intended to be further characterized, specified, or narrowed in some way, then such noun, term, or phrase will expressly include additional adjectives, descriptive terms, or other modifiers in accordance with the normal precepts of English grammar. Absent the use of such adjectives, descriptive terms, or modifiers, it is the intent that such nouns, terms, or phrases be given their plain, and ordinary English meaning to those skilled in the applicable arts as set forth above.

Further, the inventors fully informed of the standards and application of the special provisions of 35 U.S.C. § 112(f). Thus, the use of the words "function," "means" or "step" in the Detailed Description of the Invention or claims is not intended to somehow indicate a desire to invoke the special provisions of 35 U.S.C. § 112(f), to define the invention. To the contrary, if the provisions of 35 U.S.C. § 112(f) are sought to be invoked to define the inventions, the claims will specifically and expressly state the exact phrases "means for" or "step for" and the specific function, without also reciting in such phrases any structure, material or act in support of the function. Thus, even when the claims recite a "means for . . . " or "step for . . . " if the claims also recite any structure, material or acts in support of that means or step, or that perform the recited function, then it is the clear intention of the inventor not to invoke the provisions of 35 U.S.C. § 112(f). Moreover, even if the provisions of 35 U.S.C. § 112(f) are invoked to define the claimed inventions, it is intended that the inventions not be limited only to the specific structure, material or acts that are described in the illustrated embodiments, but in addition, include any and all structures, materials or acts that perform the claimed function as described in alternative embodiments or forms of the invention, or that are well known present or later-developed, equivalent structures, material or acts for performing the claimed function.

In the following description, and for the purposes of explanation, numerous specific details are set forth in order to provide a thorough understanding of the various aspects of the invention. It will be understood, however, by those skilled in the relevant arts, that the present invention may be practiced without these specific details. In other instances, known structures and devices are shown or discussed more generally in order to avoid obscuring the invention. In many cases, a description of the operation is sufficient to enable one to implement the various forms of the invention, particularly when the operation is to be implemented in software. It should be noted that there are many different and alternative configurations, devices and technologies to which the disclosed inventions may be applied. Thus, the full scope of the inventions is not limited to the examples that are described below.

The methods of the present disclosure are directed to conducting medical procedures on a body to determine the presence of, and concurrently treatable, actual or potential medical conditions that may exist at a given site of the body. The methods described here are applicable to and may be practiced in connection with any number and variety of medical procedures. By way of example and for illustrative purposes only, the methods of the disclosure are described herein with respect to procedures in the evaluation of the presence of actual or potential gynecological conditions that can be readily treated in real time.

As used herein, the phrase "medical condition" means any type of condition or occurrence in a body that can be detected through visual observation. Such medical conditions or occurrences may, most typically be, conditions that are manifested in the epidermal layers of the body, including the epithelium, but which may also extend into dermal and subcutaneous layers of the skin. Such conditions may also be located in or one organs of the body. The term "medical condition" is also used herein to refer to conditions that may be categorized as existential disease conditions or conditions that are merely indicative of potential disease conditions that may be suitable for treatment prophylactically. Similarly, the term "gynecological conditions" as used herein means observable events on or in the epithelial tissue of the vagina, cervix or uterus that are categorized as actual disease conditions or are potential disease conditions, such pre-cancerous cells or lesions. No limitation is to be implied by the general terms "medical condition" or "gynecological condition."

In general, methods of this disclosure are directed to concurrent detection and treatment of actual or potential medical conditions of a body, meaning those conditions that can be detected and evaluated as being treatable and then being treated immediately following detection and evaluation, thereby avoiding multiple patient treatment events. The methods of the disclosure comprise placing a guide device in proximity to a site of a body to be evaluated for detection of actual or potential medical conditions. Guide devices that are usable in the disclosed methods include any instrument that facilitates placement of other medical instruments or devices into the body and/or which may improve visualization of a site. For example, such guide devices may include cannulas that are placed through openings formed in the body or placed directly into body cavities, such as the ears, nose, throat, urethra, vagina or rectum. Other suitable guide devices may include scopes having one or more lumens for passing instruments therethrough.

The methods of the disclosure further comprise placing a detection device in proximity to the site of the body to be evaluated using the guide device, as necessary, to aid placement of the detection device. That is, a guide device may not always be necessary for facilitation of placement of a detection device and, indeed, some detection devices may provide a guide device in tandem therewith. The detection device may be any instrument or material aspect that can aid the health care professional in evaluating the site for the presence of an actual or potential medical condition, or disease condition. One example of a detection device suitable for use in the methods of the disclosure are visualization instruments, such as scopes or instruments that have a camera element for visualizing, in real-time, a site of the body for evaluation.

Other or additional detection devices may include devices that deliver to the site a detector material that is selected to detect one or more actual or potential medical conditions at the site following the placing of the detection device in proximity to the site. By way of example, a detector device may be used that is structured to deliver a detector material, such as a flowable substance, to the site for facilitating the evaluation and detection of a condition. Such detector materials, when applied to epithelial cells, stain pre-cancerous cells so that the cells can be evaluated and removed. The detector device may be configured to deliver the detector material by means of spraying or contact with an applicator device that is saturated with the detector material, such as a swab. Consequently, as used herein, "flowable substance" refers to any material that is sufficiently fluid to be applied by spraying or a substance that is thicker or more viscous that can be applied by an applicator device.

In certain methods of the disclosure, the detector device may comprise a tubular member having a swab attached at one end thereof. The tubular member defines a lumen for delivering one or more substances through the lumen to the swab attached at the end of the lumen.

In accordance with the methods of the disclosure, a determination is made by the health care professional, by aid of the detection device, of the presence of an actual or potential medical condition at the site. If it is determined that a medical condition exists, such as the presence of pre-cancerous cells, the health care professional can then determine if the medical condition is concurrently treatable, while the aforementioned instrumentation is in place. If immediate treatment is possible and advisable, placement of a treatment device at the site is made. Placement of the treatment device may be made using the guide device to facilitate placement of the treating device in proximity to the site.

The site, having been evaluated and the presence of a medical condition being confirmed, treatment is then made. What treatment devices may be used in the methods are dependent upon the nature of the actual or potential medical condition that is detected. Most typically, treatment devices may include excising tools, such as scalpels or scopes having a blade at one end. Treatment devices may also include cryogenic tools that dispense liquid nitrogen or a similar material that has the ability to freeze and/or destroy tissue upon contact. Other devices that treat the specific medical condition are suitable for use.

Once the medical condition has been treated in situ, the treatment device is removed, followed by removal of the detection device, if still in place, then followed by removal of the guide device from the site. Notably, the positioning and the removal of the guide device, detection device and treatment device may be in a different sequence than specifically described herein. The order in which certain elements or steps of the methods are made may vary depending on the circumstances of the procedure being conducted.

In a specific example of the methods of the disclosure, the method may be used in the evaluation and treatment of actual or potential gynecological conditions in real-time. This is a particularly important achievement since gynecological procedures can be painful for a patient, in terms of both physical pain and the anxiety that comes from having to wait for laboratory results and potential treatment. The ability to conduct gynecological procedures to determine the presence of actual or potential medical conditions and immediately treat the condition, if detected, is significant in relieving concern for the patient and in reducing costs and time expenditure.

In methods of evaluating and concurrently treating actual or potential gynecological conditions, a guide device may be employed in the form of a speculum, inserted into the vagina, to facilitate visualization and insertion of other devices for carrying out various procedures. A spiral cervical retractor device may then be positioned using the speculum as a guide. A spiral cervical retractor of the type disclosed in U.S. Pat. No. 6,537,285 may be used to manipulate the cervix for better alignment and/or improved visualization of the site. The spiral cervical retractor device may also provide additional guide members, in the form of lumens, which can be used in placement of additional instruments and devices.

A detector device is then placed using, if necessary, the guide device or spiral cervical retractor device. The detector device is used for determining the presence of any gynecological conditions that may require treatment. Such detector devices may include visualizing scopes having optic devices. Detector devices may also include applicator devices, such as swabs or sprayers, which can deliver to a site a detector material that, upon contact with the tissue at a site, will indicate the presence of a gynecological condition or the potential for a condition.

In one embodiment of this method, a swab may be used which has a tubular member providing a lumen through which a liquid detector material and/or other substance or medicament can be delivered to the site. One such liquid detector material is acetic acid. Using and applying a 3-5% acetic acid solution to the cervix will cause suspicious lesion to turn acetowhite, visually indicating a positive presence of premalignant or cancerous cells, that can be detected by visual inspection by the caregiver. These lesions can be immediately treated as herein described. In addition, biopsies can be taken from suspicious acetowhite positive lesions and sent to a lab for further testing if necessary. Such visual inspection using acetic acid solutions are a more accurate form of lesion detection than Pap tests, are less expensive and according to the present invention allow for the immediate treatment of such lesions. Other detector materials that highlight such lesions in situ so as to be visually detectable may also be used in accordance with the present invention.

That is, one or more materials can be introduced to, or even mixed within, the lumen for delivery to the swab portion at the end of the tubular member, and the swab can then be contacted with the tissue at the site to deliver the material or substance. In certain embodiments, the swab device may be pre-filled with a material for ease of use.

Once the site has been evaluated for the presence of an actual or potential gynecological condition, the health care professional can then make a determination of whether immediate treatment of the condition is warranted. A treatment device is then positioned, by means of the guide device or spiral cervical retractor device, at the site and treatment of the condition is made. The treatment device can be any number of instruments, selected in accordance with the nature of the procedure, and may include excising devices having a cutting tool at one end or a cryogenic device that can deliver a substance to the tissue which will freeze and/or destroy the tissue deemed to present a treatable condition.

Once treatment has been affected, the treatment device is removed, followed by removal of the spiral cervical retractor device and removal of the speculum. Insertion and/or removal of these devices may be made in an order other than previously described and may be dictated by the nature of the procedure being conducted.

As shown in FIG. 1, a method for concurrent detection and treatment of actual or potential medical conditions of a body is shown. The method includes the steps of placing a guide device in proximity to a site of a body to be evaluated for detection of actual or potential medical conditions. A detection device is placed in proximity to the site of the body to be evaluated using the guide device to aid placement of the detection device. The presence of an actual or potential medical condition is detected at the site that is concurrently treatable. A treatment device is placed at the site using the guide device for placement of the treating device in proximity to the site. The site of the detected actual or potential medical condition is then treated. The treatment device and guide device can then be removed from the site following treatment.

The site of the body can be contacted with a detector material selected to detect one or more actual or potential medical conditions at the site following the placing of the detection device in proximity to the site. The detector material is a flowable substance, such as a 3-5% acetic acid (or other suitable acid) solution deliverable to the site by directing the substance to or on the site by operation of the detection device. The detection device includes a tubular member having a swab attached at one end thereof. The tubular member has a lumen for delivering one or more substances through the lumen to the swab. The detection device is a scope having a visualization element for visualizing the site in real-time. The treatment device is structured with a cutting tool at one end for contacting the site and excising material from the site in response to detection of an actual or potential medical condition at the site. The amount of material excised can be to remove a detected lesion or to create a biopsy for further lab testing. The treatment device is a cryogenic tool being configured to deliver a cryogenic substance (such as liquid nitrogen) to the site for treating an actual or potential medical condition at the site. The guide device comprises a cannula portion for passing instruments therethrough to the site of the body.

Figure 2:
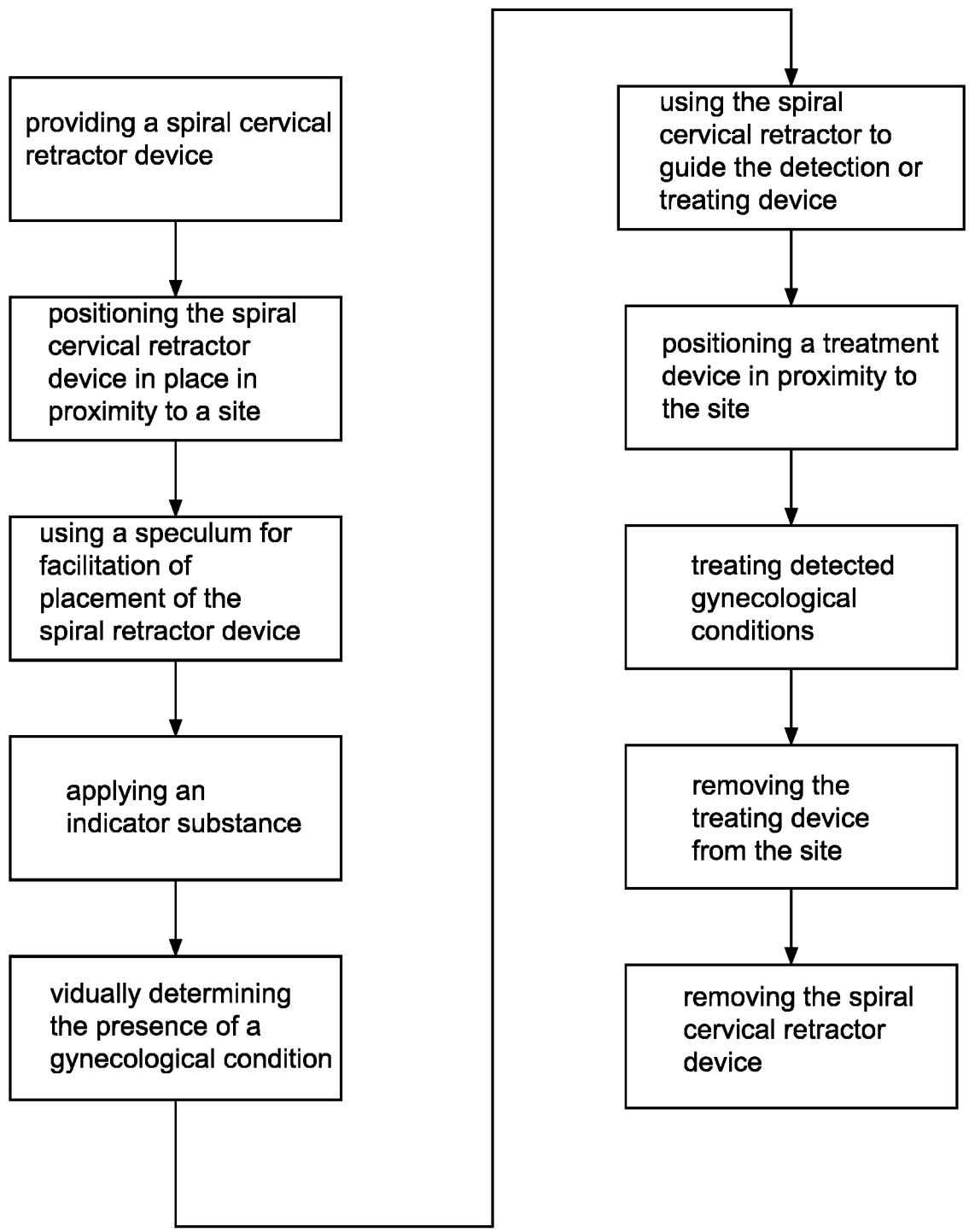
FIG. 2 is a schematic flow diagram of a second embodiment of a method for concurrent detection and treatment of actual or potential medical conditions of a body in accordance with the principles of the present invention.

FIG. 2 illustrates another embodiment of a method of evaluating and treating actual or potential conditions in real-time, specifically an actual or potential gynecological condition. The method includes providing a spiral cervical retractor device. The spiral cervical retractor device is positioned in place in proximity to a site for evaluation of actual or potential gynecological conditions. A detection device is then positioned in proximity to the site for evaluation of the presence of actual or potential gynecological conditions. The presence of an actual or potential gynecological condition is then determined by visual inspection. If a gynecological condition is visually detected, a treatment device is positioned in proximity to the site to treat detected gynecological conditions that are concurrently treatable. The detected gynecological conditions can then be sequentially treated following detection of such conditions. The treatment device and spiral cervical retractor device are then removed from the patient.

To facilitate the placement of the spiral cervical retractor device, a speculum may be used. The spiral cervical retractor is then used to guide placement of the detection device and the treating device. The presence of actual or potential gynecological conditions at the site is visually detected by use of an optical device. In order for such gynecological conditions to be detectable at the site, an indicator substance is applied to the site to highlight problematic cells and tissue that indicates the presence of actual or potential gynecological condition. As noted above, the indicator material is a flowable substance, such as a 3-5% acetic acid (or other suitable acid) liquid solution deliverable to the site by directing the substance to or on the site by operation of the detection device. The detection device includes a tubular member having a swab attached at a distal end thereof. The tubular member forms a reservoir containing the solution. A seal between the inside of the tubular member and the swab can be broken, as by bending the tube to release the solution into the swab for application to the patient. Likewise, a reservoir containing the solution could be attached to the opposite end of the tube from the swab, whereby squeezing the reservoir dispenses the solution through the tube to the swab. Thus, the tubular member has a lumen for delivering one or more substances through the lumen to the swab with the lumen prefilled with one or more substances for detecting or treating a gynecological condition at the site. The treatment device is structured with a cutting tool at one end for contacting the site and excising material from the site in response to detection of an actual or potential gynecological condition at the site. Alternatively, or in addition to, the treatment device includes a cryogenic tool configured to deliver a cryogenic substance, such as liquid nitrogen, to the site for treating an actual or potential gynecological condition at the site.

Figure 3:
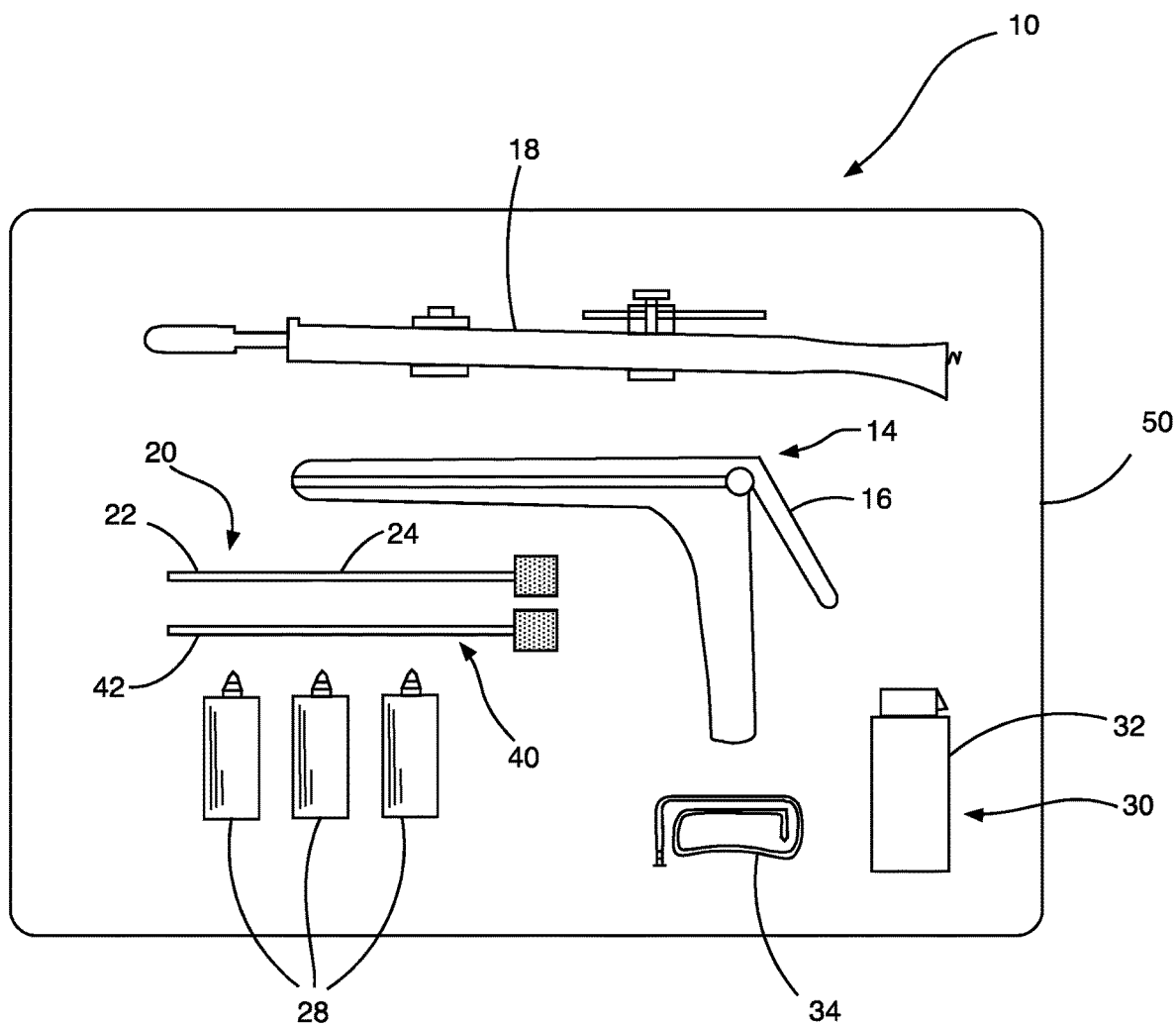
FIG. 3 is a schematic depiction of a kit comprising medical procedure devices and elements for concurrent detection and treatment of actual or potential medical conditions of a body in accordance with the principles of the present invention.

In a further aspect of the disclosure, a kit may be provided for conveniently carrying out the methods of the disclosure. FIG. 3 illustrates schematically a kit 10 that includes a guide device 14 in the form of a speculum 16, and a spiral cervical retractor 18. A detector device 20, in the form of swab device 22, is included. The swab device 22 may have a tubular member 24 providing a lumen, which may be prefilled with, for example, a detector material for application to the tissue at a procedure site. Alternatively, or additionally, vials 28 of substances or medicaments may be provided to enable the health care professional to mix substances in accordance with the nature of the procedure that is being performed.

The kit 10 also provides a treatment device 30, which may be, for example, a cryogenic device 32 in the form of a canister of liquid nitrogen and a delivery tube 34 for delivering the cryogenic material to the site. Alternatively, or additionally, another treatment device 40 may be provided in the form of a swab 42 that is prefilled or pre-loaded with a necrotizing substance that, upon contact of the swab 42 with the tissue, freezes and/or kills the tissue. The elements of the kit 10 are retained in an outer container 50, which is preferably sealed closed in a conventional manner. Other devices or instruments may be included in the kit to carry out the methods of the disclosure and the devices described are not intended to be exhaustive or limiting.

In the foregoing description of certain embodiments, specific terminology has been resorted to for the sake of clarity. However, the disclosure is not intended to be limited to the specific terms so selected, and it is to be understood that each specific term includes other technical equivalents which operate in a similar manner to accomplish a similar technical purpose. Terms such as "left" and right", "front" and "rear", "above" and "below" and the like are used as words of convenience to provide reference points and are not to be construed as limiting terms.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

In addition, the foregoing describes only some embodiments of the inventions, and alterations, modifications, additions and/or changes can be made thereto without departing from the scope and spirit of the disclosed embodiments, the embodiments being illustrative and not restrictive.

Furthermore, inventions have been described in connection with what are presently considered to be the most practical and preferred embodiments, it is to be understood that the inventions are not to be limited to the disclosed embodiments, but to the contrary, are intended to cover various modifications and equivalent arrangements included within the spirit and scope of the inventions. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment.

What is claimed is:

1. A method of evaluating and treating actual or potential gynecological conditions in real-time, comprising;
    providing a spiral cervical retractor device;
    positioning the spiral cervical retractor device in place in proximity to a site for evaluation of actual or potential gynecological conditions;
    positioning a detection device in proximity to the site for evaluation of the presence of actual or potential gynecological conditions;
    determining the presence of an actual or potential gynecological condition;
    positioning a treatment device in proximity to the site to treat detected gynecological conditions that are concurrently treatable;
    treating detected gynecological conditions sequentially following detection of such conditions;
    removing the treating device from the site; and
    removing the spiral cervical retractor device; wherein the detection device comprises a tubular member having a swab attached at one end thereof; wherein the tubular member has a lumen for delivering one or more substances through the lumen to the swab.

2. The method of claim 1, further comprising providing and placing a speculum for facilitation of placement of the spiral retractor device.

3. The method of claim 1, wherein the spiral cervical retractor is used to guide placement of the detection device and the treating device.

4. The method of claim 1, wherein determining the presence of actual or potential gynecological conditions at the site is carried out by use of an optical device.

5. The method of claim 1, wherein determining the presence of actual or potential gynecological conditions at the site is carried out by application of an indicator substance that indicates the presence of actual or potential gynecological conditions.

6. The method of claim 1, wherein the lumen is prefilled with one or more substances for detecting or treating a gynecological condition at the site.

7. The method of claim 1, wherein the treatment device is structured with a cutting tool at one end for contacting the site and excising material from the site in response to detection of an actual or potential gynecological condition at the site.

8. The method of claim 1, wherein the treatment device is a cryogenic tool configured to deliver a cryogenic substance to the site for treating an actual or potential gynecological condition at the site.

* * * * *